(12) United States Patent
Alzner et al.

(10) Patent No.: US 10,160,702 B2
(45) Date of Patent: Dec. 25, 2018

(54) PROCESS FOR THE PURIFICATION OF A CRACKING GAS STREAM IN AN OIL SCRUB COLUMN

(71) Applicant: LINDE AKTIENGESELLSCHAFT, Munich (DE)

(72) Inventors: Gerhard Alzner, München (DE); Christian Matten, Pullach (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 258 days.

(21) Appl. No.: 15/022,308

(22) PCT Filed: Aug. 5, 2014

(86) PCT No.: PCT/EP2014/002146
§ 371 (c)(1),
(2) Date: Mar. 16, 2016

(87) PCT Pub. No.: WO2015/043697
PCT Pub. Date: Apr. 2, 2015

(65) Prior Publication Data
US 2016/0229770 A1    Aug. 11, 2016

(30) Foreign Application Priority Data

Sep. 25, 2013 (EP) .................... 13004648

(51) Int. Cl.
*C07C 7/11* (2006.01)
*B01D 3/14* (2006.01)
(Continued)

(52) U.S. Cl.
CPC ............ *C07C 7/11* (2013.01); *B01D 3/143* (2013.01); *B01D 3/163* (2013.01); *B01D 3/22* (2013.01);
(Continued)

(58) Field of Classification Search
CPC ...... B01D 3/008; B01D 53/185; B01D 3/324; C10G 7/06; C10G 7/00; B01J 4/001;
(Continued)

(56) References Cited

U.S. PATENT DOCUMENTS 2,470,438 A * 5/1949 Jackson ............... B01D 3/10
                                                              261/98
5,080,837 A    1/1992 Gyokhegyi et al.
(Continued)

FOREIGN PATENT DOCUMENTS

DE    102006045498    *    4/2008
DE    102006045498 A1    4/2008
(Continued)

*Primary Examiner* — Randy Boyer
*Assistant Examiner* — Juan C Valencia
(74) *Attorney, Agent, or Firm* — Millen White Zelano & Branigan, PC

(57) ABSTRACT

A process for removing a petroleum spirit fraction and also an oil fraction from a cracking gas stream in an oil scrub column, wherein, the ratio of the amount of substance of the petroleum spirit fraction recycled into the benzene section at the top per unit time to the amount of substance of the cracking gas introduced into the oil section per unit time is in a range from 1:16 to 1:10, preferably 1:12 to 1:10.

24 Claims, 8 Drawing Sheets

(51) Int. Cl.

| | | |
|---|---|---|
| *B01D 3/16* | (2006.01) | |
| *B01D 3/22* | (2006.01) | |
| *B01D 3/28* | (2006.01) | |
| *B01D 3/32* | (2006.01) | |
| *C10K 1/18* | (2006.01) | |
| *B01D 3/26* | (2006.01) | |
| *B01F 3/04* | (2006.01) | |
| B01D 53/14 | (2006.01) | |
| B01D 53/18 | (2006.01) | |

(52) U.S. Cl.
CPC ............... *B01D 3/26* (2013.01); *B01D 3/28* (2013.01); *B01D 3/32* (2013.01); *B01D 3/324* (2013.01); *B01F 3/04241* (2013.01); *B01F 3/04255* (2013.01); *B01F 3/04468* (2013.01); *C10K 1/18* (2013.01); *B01D 53/1406* (2013.01); *B01D 53/1487* (2013.01); *B01D 53/18* (2013.01); *B01D 2252/20* (2013.01); *B01D 2256/24* (2013.01); *B01D 2257/702* (2013.01)

(58) Field of Classification Search
CPC .............. B01J 19/32; B01J 2219/32231; B01J 2219/32213; B01J 2219/3221; B01J 2219/3325; B01J 2219/00247
See application file for complete search history.

(56) References Cited

U.S. PATENT DOCUMENTS

| 5,223,183 A | 6/1993 | Monkelbaan et al. |
| 5,407,605 A | 4/1995 | Resetarits et al. |

FOREIGN PATENT DOCUMENTS

| DE | 102007056964 A1 | 5/2009 |
| WO | WO 2013/149721 A1 | 10/2013 |

\* cited by examiner

PROCESS FOR THE PURIFICATION OF A CRACKING GAS STREAM IN AN OIL SCRUB COLUMN

The invention relates to a process for the purification of a cracking gas stream in an oil scrub column.

An oil scrub column used in such a process generally has a shell which is extended along a longitudinal axis and which delimits an interior of the column, the interior being subdivided at least into a petroleum spirit section and into a separate oil section arranged below said petroleum spirit section along the longitudinal axis, there being arranged in the petroleum spirit section a plurality of first mass transfer trays, extended in particular transversely to the longitudinal axis or along the column cross section, and in the oil section a plurality of second mass transfer trays extended in particular transversely to the longitudinal axis or along the column cross section. In this oil scrub column, a cracking gas stream is firstly guided through the second mass transfer trays in the oil section and subsequently through the first mass transfer trays in the petroleum spirit section, where the second transfer trays are subjected to a liquid, hydrocarbon-containing scrubbing medium (more particularly to an oil fraction), in order to produce a mass transfer between said cracking gas stream and this second scrubbing medium, so that in the oil section an oil fraction is separated out from the cracking gas stream, and where the first mass transfer trays are subjected to a liquid, hydrocarbon-containing first scrubbing medium (more particularly to a petroleum spirit fraction), in order to produce a mass transfer between the cracking gas stream and this first scrubbing medium, so that in the petroleum spirit section a petroleum spirit fraction is separated out from the cracking gas and is drawn off in particular from there, this latter fraction having a lower boiling range than this oil fraction. According to the process of the invention a cracking gas stream is passed into the oil section and guided from bottom to top along the longitudinal axis through the second mass transfer trays, of the oil section which are arranged one above another and which are subjected to a liquid, hydrocarbon-containing second scrubbing medium in countercurrent with respect to the cracking gas stream, in order to separate out an oil fraction from the cracking gas stream, where the second mass transfer trays each have a plurality of runoff elements extending parallel to and at a distance from one another, more particularly in the form of angular profiles, which each have first and second runoff surfaces, along which the second scrubbing medium runs downward, and which converge along the longitudinal axis towards the petroleum spirit section and meet, and in so doing form an edge extending transversely to the longitudinal axis, where the cracking gas stream, after traversing the second mass transfer trays of the oil section, is passed into the petroleum spirit section, and is then guided along the longitudinal axis from bottom to top through first mass transfer trays of the petroleum spirit section, these trays being arranged one above another and taking the form of sieve trays, bubble trays or valve trays, and being fed, in countercurrent to the cracking gas stream, with a liquid, hydrocarbon-containing first scrubbing medium, in order to remove a petroleum spirit fraction from the cracking gas stream, where the cracking gas stream is drawn off from a top of the petroleum spirit section, where this petroleum spirit fraction is drawn off from the petroleum spirit section, and where a petroleum spirit fraction is recycled as first scrubbing medium into the top of the petroleum spirit section.

This problem is solved by a process according to the invention having the features described below.

Columns of the type specified above are used, for example, in the production of olefins (such as ethylene or propylene, for example), for the cooling and purification of a cracking gas stream which comprises these olefins and which is produced by thermal cracking of a hydrocarbon feedstock. In this procedure, in the presence of steam, the longer-chain hydrocarbons of the hydrocarbon feedstock are cracked thermally into shorter-chain hydrocarbons (e.g. into the desired products ethylene and/or propylene). Processes of this kind are referred to as steam cracking or pyrolysis of hydrocarbons.

The hydrocarbon feedstocks here may be very different in terms of the composition and the mixture of individual longer-chain hydrocarbons, and also in the aggregate state. Both gaseous feedstocks and liquid feedstocks are cracked, with the liquid feedstocks generally having higher proportions of longer-chain hydrocarbons and a resultant higher boiling point. Liquid feedstocks of this kind that are contemplated include, for example naphtha or gas condensates. A typical naphtha feedstock has a boiling point in the range between 160° C. and 170° C., whereas gas condensates commonly have a boiling point above 250° C.

For steam cracking, the hydrocarbon feedstock (such as naphtha, for example) is passed into the convection zone of a cracking furnace, where it is preheated in particular to 550° C. to 650° C. and converted into the gaseous phase. Hot process steam is then added to the hydrocarbon-containing feedstock vapour in the convection zone. The gaseous mixture of hydrocarbon feedstock and water vapour is passed from the convection zone into the heated cracking or pyrolysis pipes of the cracking or pyrolysis furnace. Within these heated cracking pipes, temperatures are in the range from 800° C. to 850° C., and lead to the dissociation of the longer-chain hydrocarbons from the feedstock into shorter-chain, preferably saturated hydrocarbons. The added process steam serves here for lowering the partial pressure of the individual reactants, and also for preventing reassociation of shorter-chain hydrocarbons that have already been cracked. The residence time in the cracking pipes of the cracking furnace here is typically between 0.2 and 0.6 second.

The majority of the cracking gas stream emerging with a temperature of about 850° C. from the cracking furnace consists of ethane, other olefins (propene) and diolefins, and is cooled rapidly to about 400° C., in order to prevent secondary reactions of the highly reactive cracking products. After this cooling, the cracking gas stream is supplied first to the above-elucidated oil scrub column. The purpose of this column is to cool the produced cracking gas stream further and, in a first fractionating step, to condense out a fraction composed of high-boiling hydrocarbons (e.g. oil fraction, or light oil fraction and heavy oil fraction) and of lower-boiling hydrocarbons (e.g. petroleum spirit fraction) and thereby separate this fraction from the cracking gas. In order in particular to make further use of the heat of the cracking gas within the plant, the oil fraction, or heavy oil fraction, which has been separated off has a certain minimum temperature and is employed as a heat transfer medium in other process steps in the plant.

The greatest problem in oil scrub columns of this kind is the fouling of the individual mass transfer trays as a result of formation of polymer. This polymer formation is based essentially on two mechanisms.

Firstly the condensing components comprise monomers (these are, for example, unsaturated hydrocarbons such as naphthenes, indenes or styrenes). These monomers can form polymers under certain conditions. These conditions might include a temperature range amenable to polymerization, the presence of the monomers at sufficiently high concentration, long residence times on the internals, and the presence of rust. These influences are referred to as "fouling factors". All four conditions should ideally be prevented from occurring.

Secondly the major part of the liquid hydrocarbons, which are introduced in the petroleum spirit section as the first scrubbing medium, evaporates via the petroleum spirit section on the way downwards. As a result, the smallest quantity of liquid and hence the longest residence time of the liquid is on the mass transfer trays or elements at the lower end of the petroleum spirit section. With increasing reflux, moreover, there is an increase in evaporation of the longer-chain hydrocarbons and hence in the temperature of the gaseous top product.

In prior-art oil scrub columns, therefor, there are frequent instances of polymer formation and of shifting of the lower mass transfer trays of the petroleum spirit section. Attempts have been made in the prior art to prevent these fouling problems by using side-to-side baffles in the oil section and, in the petroleum spirit section, a comparatively large number of transfer-effective mass transfer trays, in the form of sieve trays or valve trays, for example, the overall result being an oil scrub column construction of disadvantageously great height in terms of the longitudinal axis. The side-to-side baffles and column trays are single-flow or multi-flow column trays, more particularly inclined (or else horizontal) column trays, which are arranged one above another along the longitudinal axis of the oil scrub column and are each extended over a part of the column cross section, with pairs of adjacent side-to-side baffles arranged one above the other being arranged with an offset relative to one another, so that a liquid phase running off from the upper column tray impinges on the underlying column tray. Accordingly, the liquid phase flows back and forth on its way downwards in the oil scrub column.

On this basis, the problem addressed by the present invention is that of specifying a process for the purification of a cracking gas stream in an oil scrub column, which process counteracts the aforementioned fouling risk.

This problem is solved by a process having the features of Claim 1.

Provision is made accordingly for the ratio of the amount of substance of the petroleum spirit fraction recycled into the top of the petroleum spirit section, and used therein as said first scrubbing medium, to the amount of substance of the cracking gas introduced into the oil section per unit time to be in a range from 1:16 to 1:10, preferably 1:12 to 1:10.

As already elucidated at the outset, the greatest risk of fouling or shifting as a result of polymer formation exists in the lower part of the petroleum spirit section, more particularly on the lowermost mass transfer trays of the petroleum spirit section in the oil scrub column. In the prior art, attempts have been made in particular to counteract this situation by an increase in the number of mass transfer trays (more particularly in the form of sieve trays or valve trays) in the petroleum spirit section (see above), resulting in massive column lengths along the longitudinal axis. Experiments and studies have shown, however, that said polymer formation in the petroleum spirit section cannot be effectively countered by such measures.

The finding which forms a basis for the present solution according to the invention, in contrast, is that possible fouling cannot take place in the petroleum spirit section, which is more sensible in terms of the mass transfer trays, but instead in the oil section, whose mass transfer trays have a lower susceptibility to fouling.

It has emerged in this respect that it is advantageous to set the above-stated molar ratio (kmol/h) according to the invention, between petroleum spirit reflux at the top of the oil scrub column and cracking gas entry in the bottoms of the oil scrub column, in order to prevent the lower first mass transfer trays running dry and/or to prevent condensation of the unsaturated hydrocarbons (especially monomers, such as indenes, naphthenes, etc., for example) in the petroleum spirit section.

In principle it is advantageous to keep the amount of the petroleum spirit fraction that is recycled as small as necessary. Too large an amount raises the temperature of the top products of the oil scrub column. On the way downwards via the first mass transfer trays, the longer-chain hydrocarbons evaporate. The cracking gas mixture, now enriched with these evaporated longer-chain hydrocarbons, therefore has a higher boiling point than without these evaporated hydrocarbons, and so there is an increase in the equilibrium temperature on the topmost first mass transfer tray.

In summary, then, the finding underpinning the present invention is that the concentration of the unsaturated hydrocarbons (monomers such as indenes, naphthenes, etc., for example) must not take place in the petroleum spirit section, and the likelihood of the target temperature of the top product gas being achieved is in inverse proportion to the amount of petroleum spirit reflux that can be applied to the top of the column.

Furthermore, in the present case the above-described transfer-effective second mass transfer trays are used which additionally keep the polymerizable, unsaturated hydrocarbons at a distance from the first mass transfer trays (also referred to as petroleum spirit trays).

But increasing the number of mass transfer trays in the petroleum spirit part does not diminish the polymerization problem.

The sieve trays mentioned at the outset are column trays having a downcomer via which the scrubbing medium reaches column trays situated beneath, with sieve trays having a plurality of passages through which the cracking gas flows and contacts the scrubbing medium located on the respective sieve tray. Bubble cap trays may likewise have a downcomer. With bubble cap trays, moreover, the passages are bordered by chimney necks which have caps on top, the chimney necks projecting more particularly into the respectively assigned cap. Valve trays may likewise have a downcomer. With valve trays, furthermore, said passages may be closed with valves, more particularly movable and also fixed flaps or caps, which are pressed open by sufficient cracking gas pressure, allowing the cracking gas to flow upwards from below through the passages.

Moreover, the oil section, which comprises the bottoms of the oil scrub column, is extended preferably along the longitudinal axis to the petroleum spirit section, which follows on from the oil section (e.g. via said chimney tray), with the top of the petroleum spirit section forming the top of the oil scrub column, from which the cracking gas stream can be taken off after cooling and purification.

Said longitudinal axis of the oil scrub column or of the shell of the oil scrub column is extended preferably along the vertical, relative to an oil scrub column arranged in the intended way and ready for operation. The shell of the oil scrub column is of cylindrical design at least in sections, with the longitudinal axis of the oil scrub column coinciding in this case with the cylinder axis of the shell.

In accordance with one embodiment of the invention, provision may be made for a portion of the petroleum spirit fraction drawn off from the petroleum spirit section to be recycled to one of the first mass transfer trays (so-called pump-around), and specifically—based on an oil scrub column arranged in the intended manner—preferably directly to one of the lower first mass transfer trays.

This lower first mass transfer tray is preferably the second-lowermost, third-lowermost or fourth-lowermost first mass transfer tray.

Moreover, the petroleum spirit fraction is preferably drawn off from a chimney tray that separates the petroleum spirit section from the oil section, or from a lowermost first mass transfer tray that separates the petroleum spirit section from the oil section.

At one lower region of the oil section, the oil scrub column preferably has an inlet to admit the cracking gas stream, the oil scrub column—unless an oil section which is not further subdivided, or a one-circuit oil scrub, is present—being preferably designed such that the cracking gas stream fed in ascends within the oil scrub column through the second mass transfer trays arranged one above another in the oil section.

According to a further embodiment of the invention, the oil section is subdivided into a light oil section and into a separate heavy oil section, arranged below said light oil section along the longitudinal axis, where in particular the light oil section and the heavy oil section are separated from one another by means of a chimney tray. A heavy oil section is used more particularly for the treatment of cracking gas streams which have been obtained by steam cracking of relatively heavy liquid feedstocks (e.g. heavier than naphtha). In other words, then, the second section may be designed as a unitary oil section (see above) or may be subdivided into a light oil section and a heavy oil section, in which, rather than an oil fraction, a light oil fraction and a heavy oil fraction, respectively, are obtained.

When there is a heavy oil section present, the cracking gas stream is preferably passed into the column via the oil scrub column inlet now provided in the lower region of the heavy oil section, and guided through the second mass transfer trays in the heavy oil section and subsequently through the second mass transfer trays in the light oil section, where the second mass transfer trays in the heavy oil section are subjected to a liquid, hydrocarbon-containing third scrubbing medium, in order to produce mass transfer between the cracking gas stream guided through the second mass transfer trays and this third scrubbing medium, where preferably heavier hydrocarbons are separated out from the cracking gas stream, and collect as a heavy oil fraction in the bottoms of the oil scrub column.

Furthermore, the second mass transfer trays in the light oil section are preferably subjected to a liquid, hydrocarbon-containing second scrubbing medium, in order to produce mass transfer between the cracking gas stream guided through the second mass transfer trays and this second scrubbing medium. In this case, in comparison to the petroleum spirit section (see above), it is preferably predominantly higher-boiling hydrocarbons and/or, in comparison to the heavy oil section, predominantly lower-boiling hydrocarbons that are separated out from the cracking gas stream, and collect as a light oil fraction in the light oil section. In this respect, this light oil fraction is preferably drawn off from the light oil section (e.g. from a chimney tray which separates light oil section from heavy oil section), cooled, and where appropriate the fraction is purified by removing carbonaceous particles, and also recycled at least partly into the light oil section as the second scrubbing medium or as a constituent of the second scrubbing medium.

Furthermore, a part of the petroleum spirit fraction drawn off from the petroleum spirit section is preferably added to the light oil fraction drawn off from the light oil section, and this mixture is recycled as the second scrubbing medium into the light oil section, and it is reintroduced therein onto an uppermost second mass transfer tray (analogous to the oil section without heavy oil section).

Furthermore, the heavy oil fraction which is produced in the bottoms of the oil scrub column is preferably drawn off and, following cooling and optionally following removal of carbonaceous particles, it is at least partly recycled as the third scrubbing medium into the heavy oil section, and again it is introduced onto an uppermost second mass transfer tray of the heavy oil section.

The length of the petroleum spirit section is preferably not more than half of the oil section, which may optionally have a light oil section and a heavy oil section (see above).

Furthermore, according to one embodiment of the invention, the petroleum spirit section has 6 to 8, more particularly 7, first mass transfer trays. In this case, preferably, adjacent first mass transfer trays have a distance from one another along the longitudinal axis in the range from 500 mm to 900 mm.

According to a further embodiment, the oil section of the oil scrub column has 10 to 20, more particularly 16, second mass transfer trays. Where said oil section is divided into said light oil section and this heavy oil section, the light oil section preferably has 6 to 12, more particularly 8, second mass transfer trays, while the heavy oil section preferably has 4 to 8, more particularly 8, second mass transfer trays.

Adjacent second mass transfer trays of the second oil section, or of the light and heavy oil sections, of the oil scrub column preferably have a distance along the longitudinal axis in the range from 600 mm to 900 mm.

In order to distribute each of the scrubbing media to the assigned second mass transfer trays, the oil scrub column, in accordance with one embodiment of the invention, has a first liquid distributor which is arranged in the oil section and with the aid of which the second mass transfer trays are subjected to this second scrubbing medium.

According to one exemplary embodiment of the invention, this second scrubbing medium is introduced onto the edges of the runoff elements of an uppermost second mass transfer tray of the oil section by means of the first liquid distributor, so that this second scrubbing medium flows off from the respective runoff element via the runoff surfaces at both sides of the respective edge.

Where the oil section has a light oil section and a heavy oil section, said first liquid distributor is arranged in the light oil section, and this uppermost second mass transfer tray of the oil section is an uppermost second mass transfer tray of the light oil section.

A second liquid distributor is preferably arranged in the heavy oil section, with the aid of which second liquid distributor the second mass transfer trays of the heavy oil section are subjected to the third scrubbing medium. In this case, this third scrubbing medium is introduced onto the edges of the runoff elements of an uppermost second mass transfer tray of the heavy oil section by means of the second liquid distributor, so that this third scrubbing medium runs off from the respective runoff element via the runoff surfaces at both sides of the respective edge.

The first and/or the second liquid distributor preferably have in each case a plurality of cutouts, through which the respective scrubbing medium is applied to the edges of the runoff elements of the respective uppermost second mass transfer tray, the cutouts each being arranged perpendicularly above an edge of an assigned runoff element.

The second mass transfer trays of the oil section, or of the light oil and heavy oil sections, are preferably arranged one above another in such a way that the runoff elements of two adjacent second mass transfer trays are arranged with an offset relative to one another, so that the respective scrubbing medium which flows off from one runoff surface of an upper runoff element impinges on a runoff surface of a lower runoff element which is arranged beneath it with an offset. This advantageously ensures that the fill quantity of liquid is already available at the uppermost mass transfer tray, in contrast to spray nozzles, where regularly 30% to 50% of the liquid ends up in the gaps or passages between the runoff elements and becomes effective only on lower mass transfer trays.

Preferably, the liquid phase and/or the respective scrubbing medium is introduced entirely onto the runoff elements, more particularly onto their edges, by means of the first and/or second liquid distributor. Furthermore, the liquid effluent via the top of the respective column is disadvantageously greater when scrubbing medium is sprayed (small droplets).

According to one embodiment of the invention, the first and/or the second liquid distributor has a plurality of longitudinally extended final distributor channels, which are extended each transversely to the longitudinal axis or along the column cross section, and also transversely to the runoff elements or to their respective direction of longitudinal extent, over substantially the entire column cross section.

Said final distributor channels preferably each have a base which is extended transversely to the longitudinal axis and along the column cross section, and two side walls which start from said bases, are extended longitudinally and are opposite one another, said side walls each having an upper rim, with the cutouts being designed in the form of vacancies, more particularly rectangular vacancies, at the two upper rims. At the ends, moreover, the final distributor channels are preferably each bounded by a further side wall. Said vacancies or cutouts at the rims of the side walls in particular each have a lower edge, via which the liquid phase or the respective scrubbing medium is conducted out of the respective final distributor channel onto the underlying edge of a runoff element, where this lower edge is at a distance, along the longitudinal axis of the oil scrub column, from the respective base of the final distributor channel in question, meaning that the respective final distributor channel is able to collect fouling theoretically up to said lower edges of the cutouts, where the liquid phase that is to be distributed is still always able to be applied, via the cutouts and/or vacancies, to the assigned second mass transfer tray in a defined way by means of the respective final distributor channel.

Furthermore, the first and/or the second liquid distributor has at least two longitudinally extended preliminary distributor channels, arranged parallel to one another and above the final distributor channels along the longitudinal axis of the column shell, by means of which preliminary distributor channels the final distributor channels are fed with the liquid phase (e.g. oil fraction, or light oil or heavy oil fraction), where the preliminary distributor channels are extended in particular transversely to the longitudinal axis or along said column cross section. The preliminary distributor channels preferably extend transversely to the final distributor channels. The preliminary distributor channels may be connected to one another in flow terms via at least one compensation channel, thereby making it possible to compensate for for any difference in level of the liquid phase in the preliminary distributor channels by way of the at least one compensation channel.

Furthermore, the preliminary distributor channels as well preferably each have a base which is extended transversely to the longitudinal axis or along the column cross section, and two side walls which start from said bases, are longitudinally extended and are opposite one another, where said side walls each have an upper rim, where cutouts in the form of vacancies, more particularly rectangular vacancies, are designed at these rims, the liquid phase being passed into respectively one assigned final distributor channel via said cutouts. These cutouts in the preliminary distributor channels are preferably each arranged perpendicularly above an assigned final distributor channel. Here as well, said vacancies or cutouts at the rims each have a lower edge, via which the liquid phase is guided from the respective preliminary distributor channel into an underlying final distributor channel, where this lower edge is at a distance, along the longitudinal axis of the column shell, from the respective base of the preliminary distributor channel in question, so that again the respective preliminary distributor channel is able to collect fouling up to said lower edges of its cutouts, while being nevertheless able to apply the liquid phase to be distributed, via the cutouts or vacancies, onto the respectively assigned final distributor channel. Furthermore, the preliminary distributor channels are each bounded at the end by a further side wall.

Said preliminary distributor channels are preferably charged via at least one feed pipe each, preferably via two feed pipes each, with the liquid phase, i.e., with the oil fraction or with the light oil or heavy oil fraction, where these feed pipes are extended at least in sections along the longitudinal axis of the shell of the column, and so a cutout in the respective feed pipe, via which the liquid phase is delivered from the respective feed pipe, faces the respective base of the preliminary distributor channel to be supplied, along the longitudinal axis. In the region of their respective cutouts, said feed pipes are preferably arranged each between two splash plates extending parallel to one another, each of such plates being fixed in place on an assigned side wall of the respective preliminary distributor channel. Moreover, at the outwardly facing outsides of their side walls, on both sides of the cutouts in the respective preliminary distributor channel, the preliminary distributor channels have a baffle, the baffles preferably projecting vertically from the respective side wall and each projecting, by a lower free end region, into the final distributor channel arranged below the respective cutout. The baffles are designed to guide the flow of the liquid phase from the cutouts in the preliminary distributor channels, in such a way that said flow ends up as completely as possible in the assigned final distributor channel.

In the embodiment described above, therefore, the preliminary distributor and final distributor channels are preferably designed as upwardly open channels (downwardly, the channels are bounded by said bases, at the sides by said side walls, and by the other side walls on the end). Said channels are consequently also referred to as preliminary distributor and final distributor grooves, respectively.

The second mass transfer trays of the oil section, or of the light oil and heavy oil sections have the advantageous effect of allowing the generation of a multiplicity of curtains of the liquid phase (e.g. oil fraction), namely by the liquid phase flowing off from the runoff surfaces, and also, possibly, the additional effect of generating a two-phase layer on the runoff surfaces, which contributes to a high efficiency. In this respect it has emerged in tests that the mass transfer trays of the invention, also referred to as cascade trays, are comparable with dual-flow trays (these being column trays without a downcomer but with comparatively large passages, having a diameter in the range from 20 mm to 40 mm, for example, through which gas and liquid flow in countercurrent). Tests have also shown that said cascade trays or second mass transfer trays of the invention are superior in terms of capacity to the single-flow side-to-side baffles.

By virtue of their construction, the second mass transfer trays of the invention are, advantageously, unsusceptible to fouling, in the absence, for example, of any small-area openings that might rapidly become clogged. The efficiency is relatively high—according to tests, around twice as high as that of single-flow or dual-flow side-to-side baffles. Moreover, their capacity exceeds that of the side-to-side baffles. Because of the angular runoff elements, the mass transfer trays of the invention also have a comparatively high structural strength.

In the case of runoff elements in the form of angular profiles (especially those with equal arms), the runoff elements have two arms, which converge angularly along the longitudinal axis in the direction of a liquid distributor arranged above them, and meet with formation of an edge which is extended along the column cross section or transversely to the longitudinal axis. The runoff surfaces of the respective runoff element or angular profile are then formed by the upwardly turned top faces (i.e., those facing the liquid distributor) of the arms. The arms or runoff surfaces preferably include an angle in the range from 80° to 100°, more particularly an angle of 90°. The runoff surfaces additionally have a width transverse to their direction of longitudinal extent that is in the range from 40 mm to 150 mm, preferably 100 mm.

The runoff elements or their runoff surfaces (or said arms) are preferably of elongate design, meaning that along their direction of longitudinal extent they have a greater length than they do transverse to this direction, and are extended preferably over the entire column cross section, i.e. from one inside region of the shell to an opposite inside region of the shell of the oil scrub column. These runoff elements may be composed of a plurality of segments, each per se being designed as a runoff element and being arranged one after another along the direction of longitudinal extent. A gap present between two such segments (and interrupting the runoff surfaces of the composite runoff element) may be concealed by a capping element, which bears against the two runoff-surface segments of the respective segment, giving the overall impression of a uniform runoff element, which is extended in particular essentially along the entire column cross section from one inside region of the shell of the oil scrub column to an opposite inside region of the shell of the oil scrub column.

The second mass transfer trays are each extended preferably over the entire column cross section transversely to the longitudinal axis, with the runoff elements extending parallel to one another being preferably arranged equidistantly from one another transversely to their direction of longitudinal extent, meaning that pairs of adjacent runoff elements define an elongated passage or hole in the mass transfer tray, through which a gaseous phase (e.g. a cracking gas stream) is able to ascend in the column along the longitudinal axis of the column shell. Adjacent runoff elements of a second mass transfer tray here preferably have an inter-edge distance in the range from 150 mm to 300 mm. However, it is also possible for this distance to have values which deviate from this. The dimensioning of each said distance is such that the liquid phase flowing off from the runoff elements impinges on the runoff elements arranged below them.

The second mass transfer trays are preferably arranged one above another in such a way that the runoff elements of two adjacent second mass transfer trays are arranged with an offset relative to one another, with the runoff elements of the lower second mass transfer tray in each case being arranged along the longitudinal axis centrally below a passage delimited, for example, by two adjacent runoff elements of the upper second mass transfer tray.

With further preference the second mass transfer trays have a carrier ring via which the respective second mass transfer tray is fixed in place, in particular on the shell, with the carrier ring preferably running around an inside of the shell of the oil scrub column along said column cross section. The runoff elements in this case lie preferably on the carrier ring in each case by a first end region and by an opposite, second end region. In this arrangement, one of the end regions is mounted on the carrier ring via a fixed bearing, the other end region via a sliding bearing. Where one runoff element consists of a plurality of segments, there is one fixed bearing per segment; the other bearings of the segment in question are sliding bearings.

Furthermore, the runoff elements may be supported by one, two or more bearers (more particularly profiled bearers) which extend parallel to one another and are extended along said column cross section, these bearers extending transversely to the runoff elements and being members on which the runoff elements and/or their components (see above) lie. With their opposite end regions, such bearers preferably each engage beneath the carrier ring, and are each joined on one side, via a sliding bearing arranged beneath the carrier ring, to the shell, and on the other side via a fixed bearing arranged beneath the carrier ring.

Further details and advantages of the invention will become apparent from the descriptions below of exemplary embodiments by means of the figures.

Figure 1:
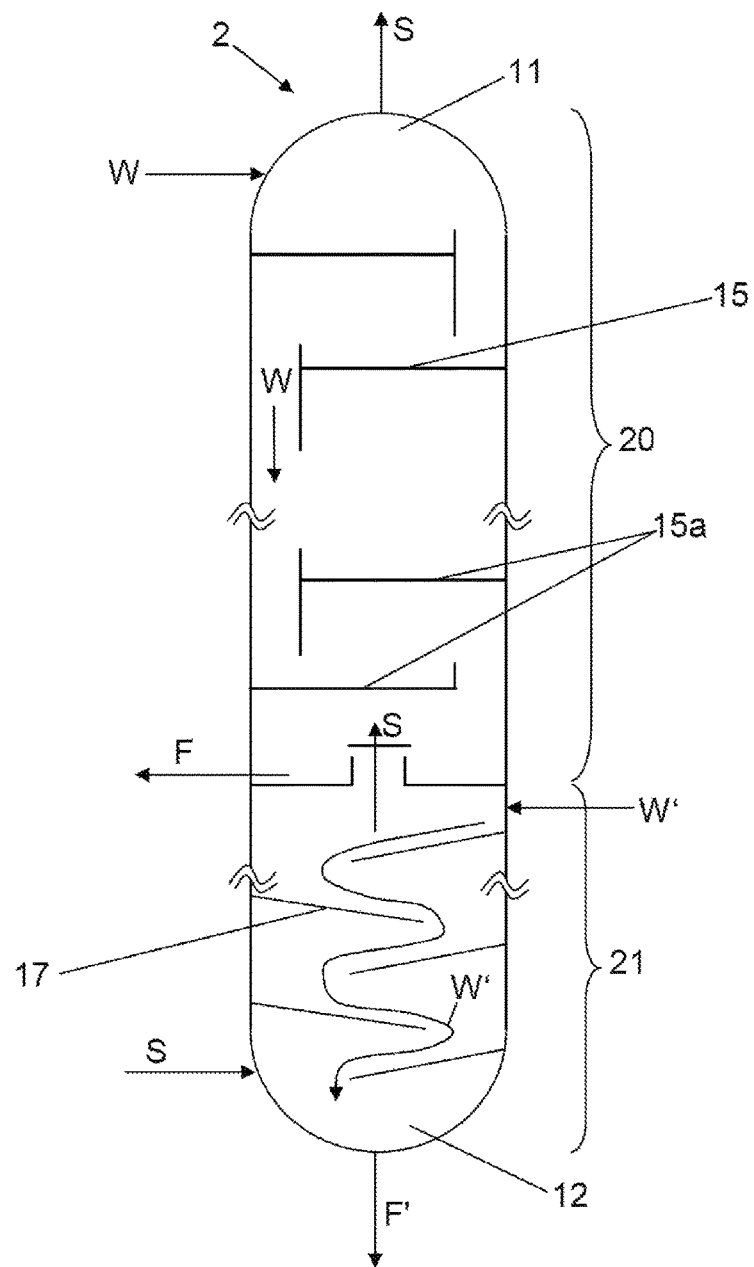
FIG. 1 shows a schematic sectional view of a prior-art oil scrub column.

FIG. 1 shows a prior-art oil scrub column 2. The oil scrub column 2 has an upper petroleum spirit section 20 and a lower oil section 21; a cracking gas stream S, produced by steam cracking of a hydrocarbon feedstock (e.g. naphtha) (see above), is passed into a lower region of the oil section 21. In the oil section 21, the cracking gas stream S is subjected in countercurrent to a liquid, hydrocarbon-containing second scrubbing medium W', which in the oil section 21 is applied to second mass transfer trays in the form of single-flow side-to-side baffles 17. As a result, higher-boiling hydrocarbons are separated out from the cracking gas stream S, and collect as oil fraction F' in the bottoms 12. In the petroleum spirit section 20, the cracking gas stream S is contacted with a first scrubbing medium W by means of first mass transfer trays, in the form of sieve trays or valve trays 15, to which the liquid, hydrocarbon-containing first scrubbing medium W is applied, in order to separate out from the cracking gas stream S a comparatively lower-boiling petroleum spirit fraction F.

Figure 2:
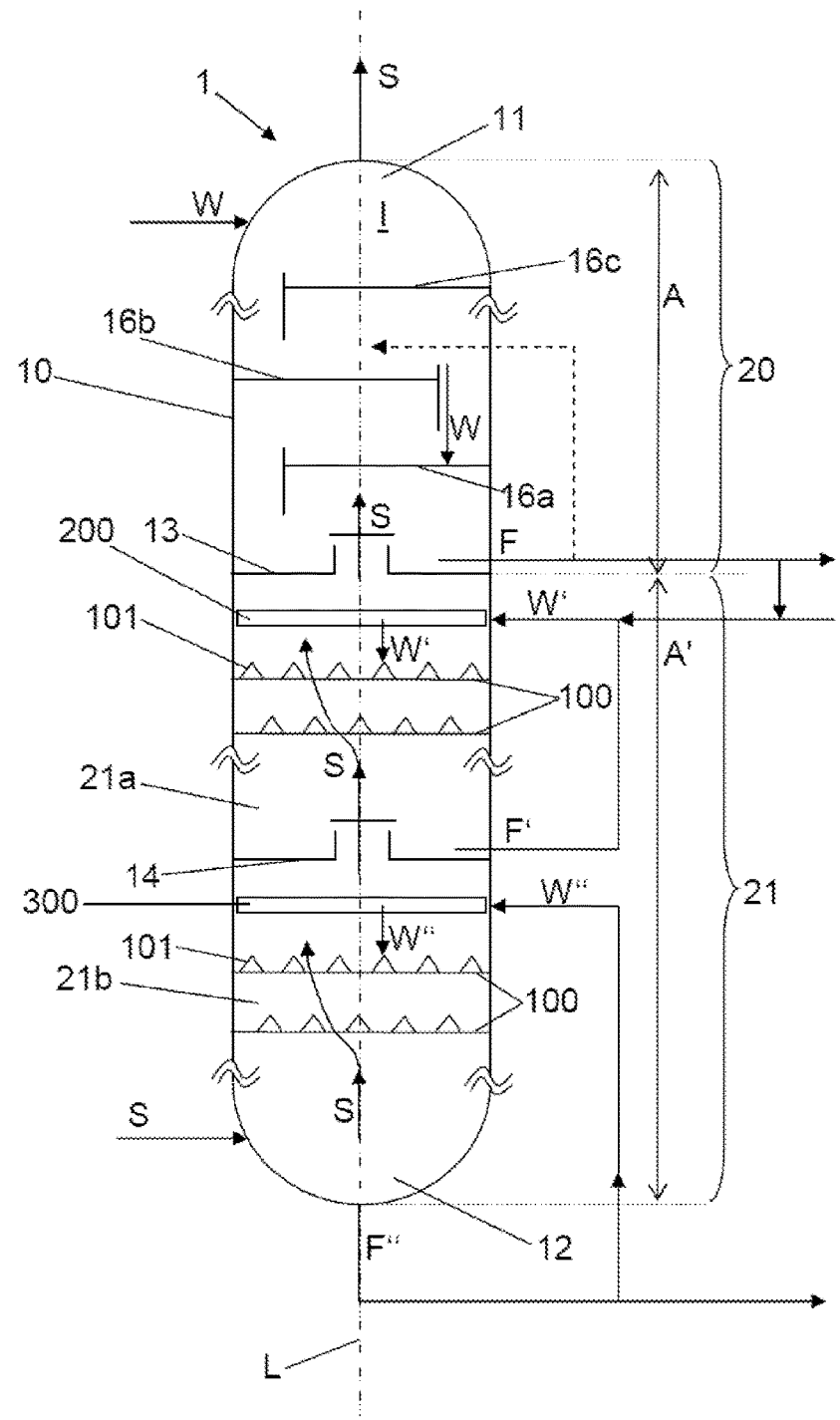
FIG. 2 shows a schematic sectional view of an oil scrub column for carrying out the inventive process.
Figure 3:
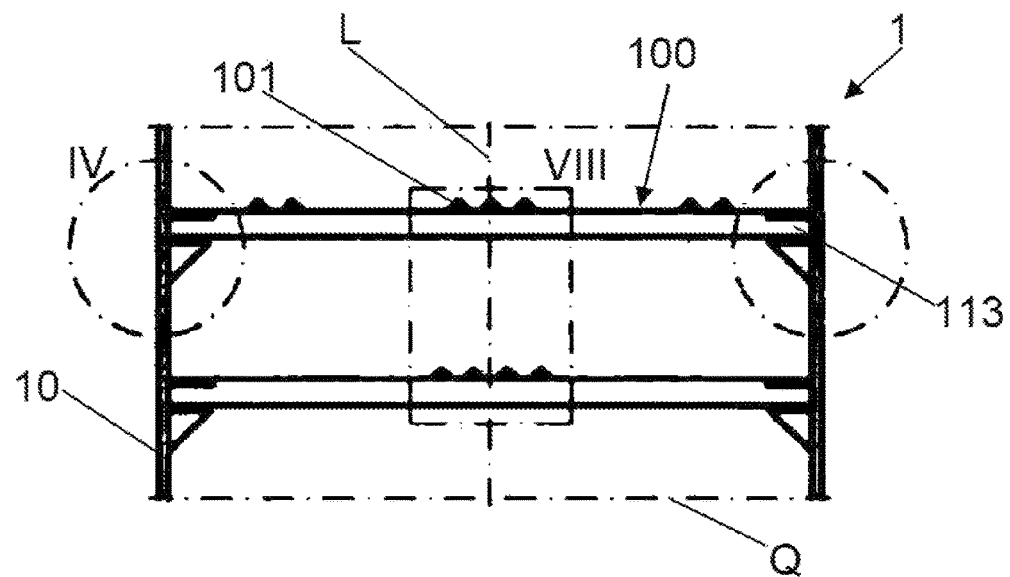
FIG. 3 shows a detail from FIG. 2.
Figure 4:
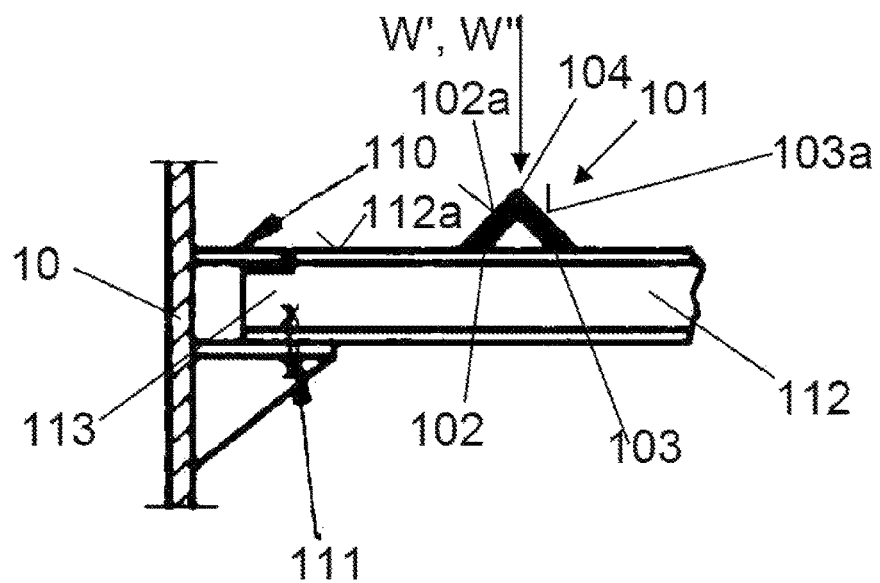
FIG. 4 shows the detail IV from FIG. 3.
Figure 5:
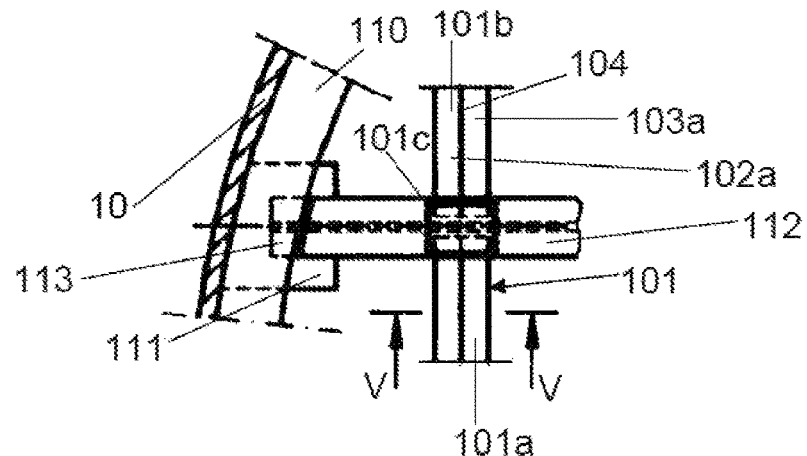
FIG. 5 shows a plan view of the detail as per FIG. 4.
Figure 6:
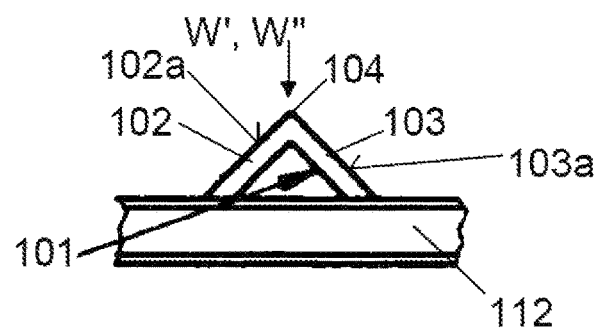
FIG. 6 shows a partial sectioned view along the line VI-VI in FIG. 5.
Figure 7:
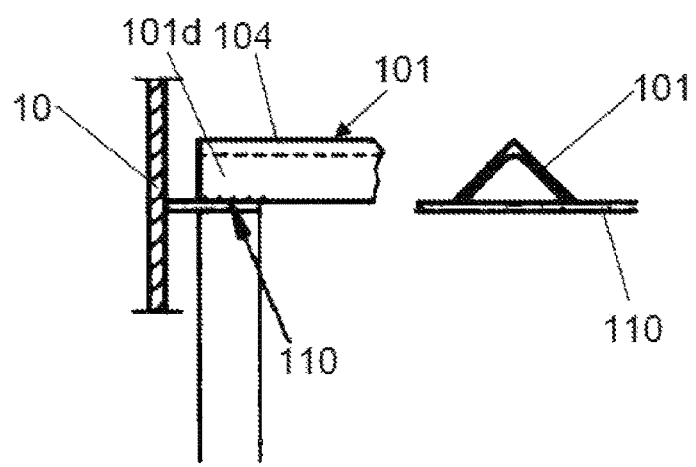
FIG. 7 shows a detail view of a fixed bearing of an inventive runoff element.

The inventive process which is explained by way of example on the basis of the oil scrub column 1 according to FIG. 2, for its part, is designed so that fouling on the lower first mass transfer trays 15a of the oil scrub column 2 as per FIG. 1 is counteracted.

In detail, the oil scrub column 1 according to FIG. 2 has a substantially cylindrical shell 10, which is extended along a longitudinal axis L coincident with the vertical and which delimits an interior I of the oil scrub column 1, which is subdivided along the longitudinal axis L into a petroleum spirit section 20, comprising the top 11 of the oil scrub column 1, and into an oil section 21, which is arranged below it and comprises the bottoms 12 of the oil scrub column 1, said section 21 being able to be subdivided into a light oil section 21a and, arranged beneath it, a heavy oil section 21b. The petroleum spirit section 20 here is separated by a chimney tray 13 from the oil section 21 or light oil section 21a, and the light oil section 21a is separated by a chimney tray 14 from the heavy oil section 21b.

The precooled cracking gas stream S is supplied at a temperature between, for example, about 400° C. and 600° C. to the oil scrub column 1 in the base region of the heavy oil section 21b. The heavy oil section 21b of the oil scrub column 1 has a plurality of second mass transfer trays 100, which are arranged one above another along the longitudinal axis L and are shown in FIGS. 3 to 9. As described above, adjacent second mass transfer trays 100 are each designed so that the runoff elements 101 of each lower second mass transfer tray 100 are arranged centrally below the passages or holes in the second mass transfer tray 100 arranged above it.

The cracking gas S flows through the entire interior of the oil scrub column 1 from bottom to top along the longitudinal axis L of the shell 10 of the column 1; in the heavy oil section 21b, a liquid, hydrocarbon-containing third scrubbing medium W" is introduced onto the second mass transfer trays 100 by means of a second liquid distributor 300, which is shown in FIGS. 9 to 14 and which is arranged above the second mass transfer trays 100 along the longitudinal axis L. The third scrubbing medium W" flows down correspondingly in the heavy oil section 21b and is brought into intense contact with the ascending cracking gas stream S by the second mass transfer trays 100. As a result, the fraction of the heaviest hydrocarbons is separated out from the cracking gas stream S, and these hydrocarbons collect as liquid heavy oil fraction F' in the bottoms 12 of the oil scrub column 1. From there, the heavy oil fraction F''' is drawn off, cooled and recycled as a third scrubbing medium W''' at least partly into the heavy oil section 21b, and is again introduced by means of the second liquid distributor 300 onto an uppermost second mass transfer tray 100 or onto the cracking gas phase S.

From the heavy oil section 21b, the cracking gas stream S, depleted of the heavy oil fraction, passes via the chimney tray 14 into the light oil section 21a of the oil scrub column 1. Here, the cracking gas phase S continues to ascend upward, likewise through second mass transfer trays 100, which are subjected in countercurrent, via a first liquid distributor 200 (see FIGS. 9 to 14) of the light oil section 21a, to a liquid, hydrocarbon-containing second scrubbing medium W', with the result that corresponding lower-boiling hydrocarbons separated out from the gas phase S collect as a liquid light oil fraction in the light oil section 21a, more particularly on the chimney tray 14. From there, this light oil fraction may pass, optionally via runoffs, directly into the preliminary distributor channels 210 of the second liquid distributor 300 of the heavy oil section 21b. Furthermore, said light oil fraction F' is drawn off from the light oil section 21a, cooled, and mixed with a petroleum spirit fraction F drawn off from the petroleum spirit section 20, and recycled as the second scrubbing medium W', via said first liquid distributor 200, into the light oil section 21a.

From the light oil section 21a, finally, the cracking gas stream S, depleted of the light oil fraction F', passes via the chimney tray 13 into the petroleum spirit section 20 of the oil scrub column 1, where the cracking gas stream S passes via first mass transfer trays 16a, 16b, 16c, in the form of sieve, bubble cap or valve trays (cf. FIGS. 15 to 17), into the top 11 of the column 1, from where it is drawn off. In the petroleum spirit section 20, the cracking gas stream S is contacted with a liquid, hydrocarbon-containing first scrubbing medium W, which is introduced onto the first mass transfer trays 16a, 16b, 16c, with the consequence that lower-boiling hydrocarbons are separated out from the cracking gas stream S and collect as a liquid petroleum spirit fraction F in the petroleum spirit section 20. The petroleum spirit fraction F is drawn off from the petroleum spirit section 20 and mixed partly with the light oil fraction F' drawn off from the light oil section 21a, and is recycled as second scrubbing medium W' into the light oil section 21a (see above). Furthermore, a part of the petroleum spirit fraction F may be recycled (so-called pump around) to one of the lower first mass transfer trays, e.g. to the second lowest first mass transfer tray 16b from the bottom, in order to increase the circulation on the lower first mass transfer trays 16a, 6b, thereby counteracting shifting of the lower first mass transfer trays 16a, 16b which are particularly susceptible to fouling as a result of formation of polymer (see above).

Furthermore, in accordance with the invention, a petroleum spirit fraction F as scrubbing medium W or as a constituent of the scrubbing medium W is recycled to the top 11 of the oil scrub column 1 or of the petroleum spirit section 20, with the ratio between this petroleum spirit reflux (kmol/h) and the amount of substance of cracking gas S fed into the oil section 21 or heavy oil section 21b (kmol/h) being between 1:16 and 1:10, preferably between 1:12 to 1:10. The petroleum spirit fraction recycled to the top 11 (and referred to as reflux) comes preferably from a water scrub column downstream of the oil scrub column 1, and passes from the bottoms of said water scrub column into a petroleum spirit/water separating vessel, from which it is applied, preferably in water-free form, as reflux to the top 11 of the oil scrub column 1. When the plant is started up, external petroleum spirit may additionally be applied to the top 11 of the oil scrub column 1 (see above).

Along the longitudinal axis L, the petroleum spirit section 20 of the oil scrub column 1 preferably has a length A which is smaller than the length A' of the oil section 21, preferably less than half the length A' of the oil section 21.

Where the cracking gas S is generated by steam cracking a feedstock such as naphtha or a lighter feedstock, the heavy oil section 21b can be omitted. In that case an oil fraction F' is drawn off from the bottoms 12 of the oil section 21, and is treated in the same way as for the light oil fraction F' in the exemplary embodiment above.

FIGS. 3 to 9 show the second mass transfer trays 100 in detail. Generally speaking, mass transfer trays 100 of these kinds can be used advantageously anywhere in columns where there is a high risk of fouling as a result of the liquid or gaseous phases between which mass transfer is to take place.

Figure 9:
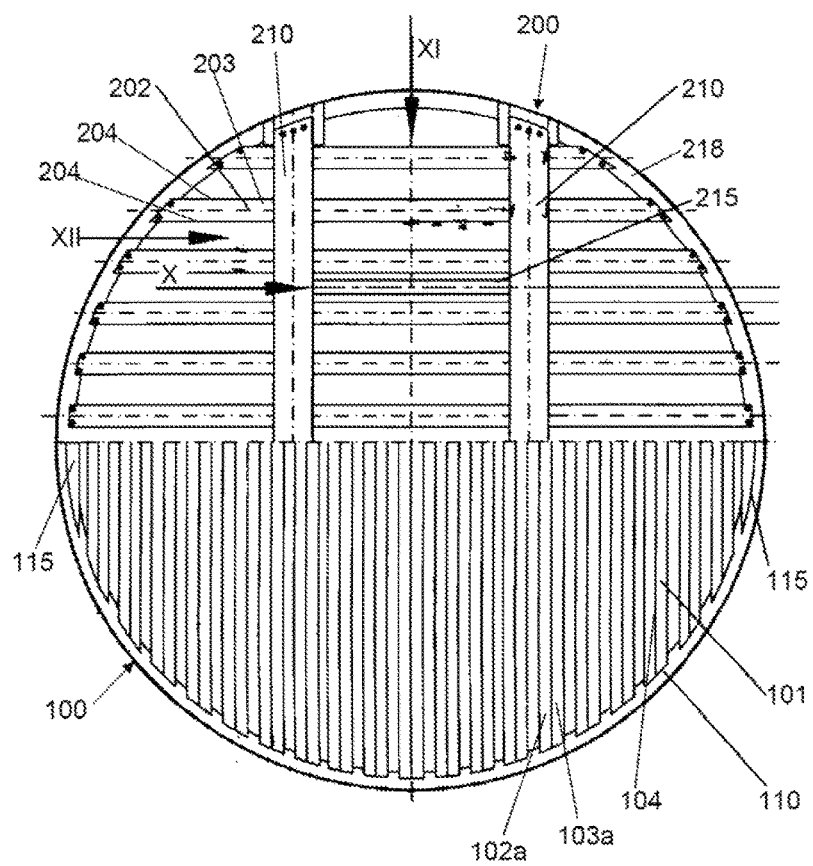
FIG. 9 shows a plan view of an inventive mass transfer tray (lower part) and of a liquid distributor (upper part) for applying a liquid phase to the mass transfer tray.

In accordance with FIG. 9, the second mass transfer trays 100 have a plurality of longitudinally extended runoff elements 101, which are oriented parallel to one another and are extended parallel to the column cross section Q, which extends vertically relative to the longitudinal axis L, at the same height (based on the longitudinal axis L of the shell 10). Adjacent runoff elements 101 here are spaced apart from one another equidistantly and transversely to their direction of longitudinal extent, thus forming a passage or hole between each pair of runoff elements 101, through which gaseous phase S is able to ascend in the interior of the oil scrub column 1.

In accordance with FIGS. 4 to 7 and 9, the runoff elements 101 each have first and second arms 102, 103, which are joined angularly to one another to form an edge 104, so that the runoff elements 101 form equal-armed angular profiles 101. The respective edges 104 of the runoff elements 101 are likewise of longitudinally extended design, and extend parallel to the column cross section Q. Moreover, the arms 102, 103 of the runoff element 101 converge upwardly on one another along the longitudinal axis L, meaning that the two arms 102, 103 of a runoff element 101 each define an upwardly facing runoff surface 102a, 103a, each of which drops downwards, starting from the edge 104 of the respective runoff element 101. If, correspondingly, the respective liquid scrubbing medium W', W" is introduced by a first or second liquid distributor 200, 300 onto the respective edge 104 of a runoff element 101, it flows off downwards via the runoff surfaces 102a, 103a at both sides of the respective edge 104, thereby forming two curtains of the scrubbing medium W', W" in question.

Figure 8:
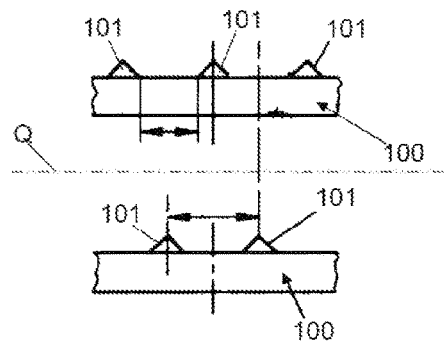
FIG. 8 shows a selected sectional view of the detail VIII as per FIG. 3.

In accordance with FIG. 8, a plurality of inventive second mass transfer trays 100 are arranged one above another along the longitudinal axis L, the runoff elements 101 of adjacent second mass transfer trays 100 being arranged with an offset relative to one another along the column cross section Q, and so the liquid phase W', W", running off from the runoff surfaces 102a, 103a of the respective runoff element 101 of a second mass transfer tray 100 is introduced onto two runoff elements 101, arranged below this runoff element 101, of an underlying second mass transfer tray 100. Here, the runoff elements 101 of the lower second mass transfer tray 100 in each case are arranged along the column cross section Q, preferably in each case centrally, between two runoff elements 101 of the second mass transfer tray 100 situated above it. The inventive second mass transfer trays 100 are therefore also called cascade trays.

In accordance with FIGS. 4-7, the runoff elements 101 of a second mass transfer tray 100 lie, with mutually opposite end regions 101d (cf. FIG. 7), on an assigned, circulating carrier ring 110, which is fixed in place on an inside of the shell 10 of the oil scrub column 1. Here, one end region 101d in each case is mounted via a fixed bearing, the other via a sliding bearing, on the carrier ring 110.

The runoff elements 101 may be extended comprehensively over the column cross section Q from one inside region of the shell 10 of the oil scrub column 1 to an opposite inside region of the shell 10 of the oil scrub column 1. Also possible, however, is for a runoff element 101 to consist of a plurality of segments 101a. 101b (cf. FIG. 5), which are arranged one after another along the direction of longitudinal extent of the runoff element 101. In this case, gaps between two adjacent segments 101a, 101b may be covered over by a cap 101c. In that case, such segments 101a, 101b lie by their free end regions on the carrier ring 110 and/or on a bearer 112, more particularly a profiled bearer 112, which is extended transversely to the runoff elements 101. Optionally it is possible to provide a plurality of such bearers 112, which in that case extend parallel to one another. One end region of a segment 101a, 101b is then mounted via a fixed bearing on the carrier ring 110 or on a bearer 112, the other end region, respectively, via a sliding bearing.

The bearers 112, where present, engage by one free end region 113 each beneath the carrier ring 110, said region lying on a bearing 111 fixed in place beneath the respective carrier ring 110 on the inside of the shell 10. These end regions 113 of the respective bearer 112 have a vacancy to accommodate the assigned carrier ring 110, and so the respective carrier ring 110, together with the respective bearer 112, forms a substantially stepless surface 112a, on which the runoff elements 101 may lie (cf. FIG. 4). In the case of the bearers 112, in each case, likewise preferably, one end region 113 is mounted via a bearing 111 in the form of a sliding bearing 111 (cf. FIG. 4) on the shell 10, whereas the other end region 113 is mounted via a fixed bearing (cf. FIG. 3).

Furthermore, in accordance with FIG. 9, the second mass transfer trays 100 may each have, to the side of an outermost runoff element 101, a cover element 115, whose purpose is to delimit the passage between said runoff element 101 and the cover element 115 to the envisaged width.

To subject the second mass transfer trays 100, arranged one above another, to the respective liquid scrubbing medium W', W", in accordance with FIGS. 2 and 9-14, a first and/or second liquid distributor 200, 300 is provided. These distributors each have a plurality of upwardly open end distributor channels 202, which are box-shaped in cross section, which are arranged above the respectively assigned second mass transfer trays 100 along the longitudinal axis L of the oil scrub column 1, and which are each extended along said column cross section Q and also transversely to the runoff elements 101.

The longitudinally extended final distributor channels 202 each have a base 203, which is extended parallel to the column cross section Q, and also two side walls 204, said side walls 204 starting from said base 203 and each having an upper rim 205 (cf. FIG. 11), along which cutouts 201 are designed in the form of rectangular vacancies, which along the longitudinal axis L of the respective column 1, 3, 4 are arranged each perpendicularly above an edge 104 of a runoff element 101 assigned to the respective cutout 201. To distribute the liquid phase W', W" onto the runoff elements 101, the final distributor channels 202 are then charged with the liquid phase W', W" in such a way that it passes over the lower edges 206, extending parallel to the respective tray 203, of the individual cutouts 201 and falls down onto said edges 104, and is distributed further downward by the cascaded runoff elements 101 (cf. FIG. 8), thus forming a multiplicity of curtains of the liquid phase W', W", through which a gaseous phase for treatment (e.g. cracking gas) S is forced in countercurrent, thereby occasioning an intense mass transfer and/or energy transfer between the phases W', W" and S.

Figure 10:
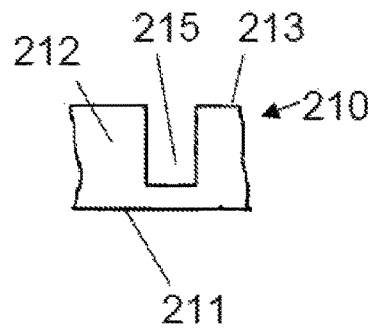
FIG. 10 shows a selected view along the direction X of FIG. 9 of a compensation channel of the liquid distributor, which joins two preliminary distributor channels of the liquid distributor to one another.
Figure 11:
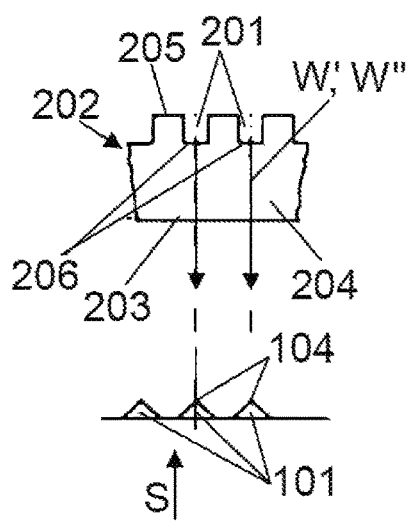
FIG. 11 shows a selected view along the direction XI of FIG. 9 of a final distributor channel with cutouts in the form of rectangular vacancies, which are designed along one rim of a side wall of the final distributor channel.
Figure 12:
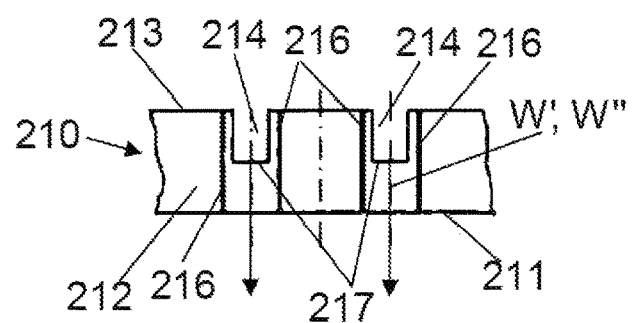
FIG. 12 shows a selected view along the direction XII of FIG. 9 of a preliminary distributor channel with cutouts in the form of rectangular vacancies, which are designed along one rim of a side wall of the preliminary distributor channel.

For the purpose of charging the final distributor channels 202 with the liquid phase W', W", in accordance with FIG. 10, two preliminary distributor channels 210 are provided, which are parallel to one another and are arranged above the final distributor channels 202 along the longitudinal axis L, said channels 210 likewise being designed upwardly open and being box-shaped in cross section. The preliminary distributor channels 210 likewise are extended along the column cross section Q, preferably, in the same way as for the final distributor channels 202, over essentially the entire column cross section, i.e., from one inside region of the shell 10 of the respective column 1, 3, 4 to an opposite inside region of the shell 10. Furthermore, the preliminary distributor channels 210 are extended transversely to the final distributor channels 202.

The preliminary distributor channels 210 likewise each have a base 211, which is extended parallel to the column cross section Q, and also two side walls 212, which start from said base 211 and which each have an upper rim 213, at which cutouts 214 are designed in the firm of rectangular vacancies, via which the liquid phase W', W" can be passed into one assigned final distributor channel 202 in each case. For this purpose, the cutouts 214 of the preliminary distributor channels 210 are in turn each arranged perpendicularly, along the longitudinal axis 1 of the shell 10 of the respective column 1, 3, 4, above an assigned final distributor channel 202 (cf. FIGS. 12, 13 and 14).

Figure 13:
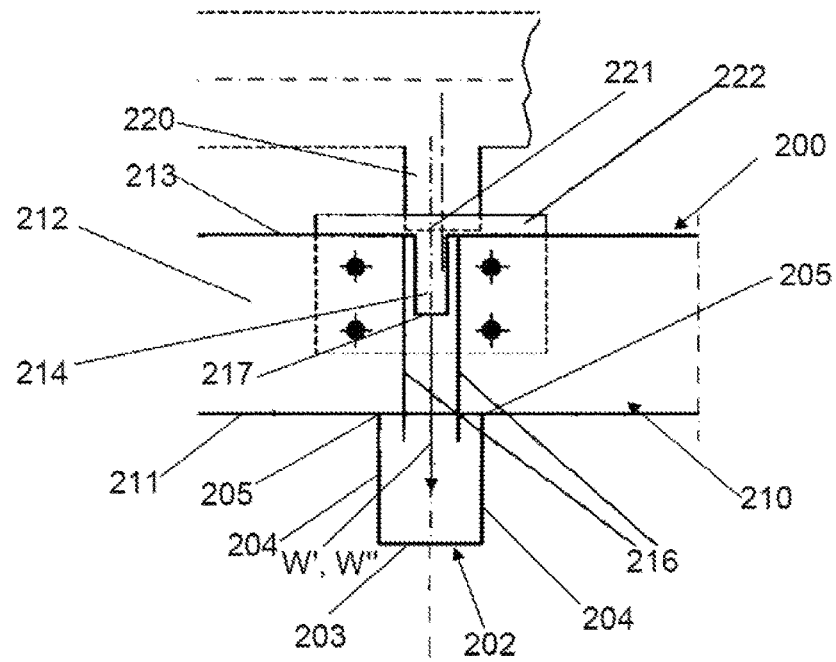
FIG. 13 shows a selected, partially sectioned view of a feed pipe for a preliminary distributor channel of a liquid distributor as per FIGS. 9 to 12.
Figure 14:
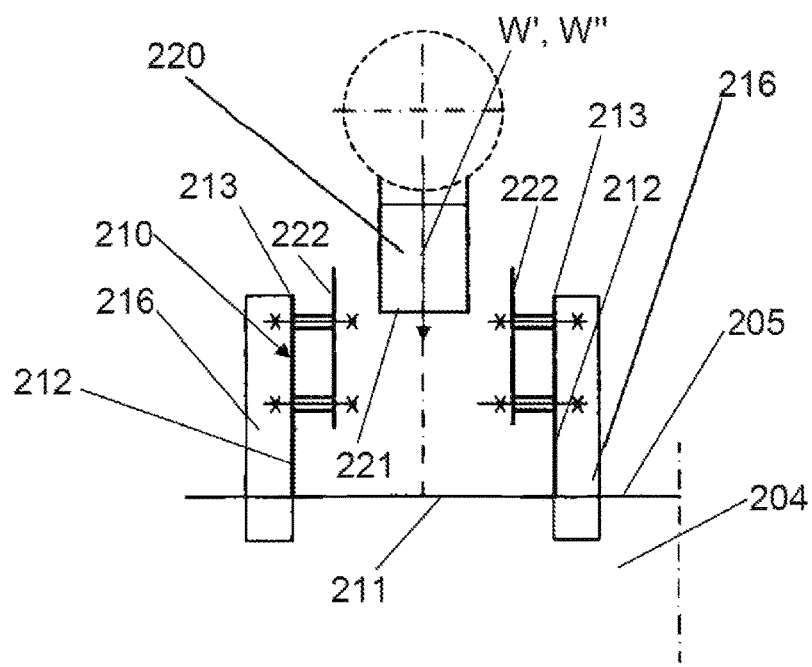
FIG. 14 shows a further selected, partially sectioned view of a feed pipe for a preliminary distributor channel of a liquid distributor as per FIGS. 9 to 13.

In accordance with FIGS. 13 and 14, in turn, said preliminary distributor channels 210 are charged, via at least one feed pipe 220, preferably via two feed pipes 220, with the liquid phase F, said pipes 220 extending at least in sections along the longitudinal axis L of the shell 10 of the respective column 1, 3, 4; a cutout 221 of the respective feed pipe 220, via which the liquid phase W', W" flows from the respective feed pipe 220 into the assigned preliminary distributor channel 210, faces the respective base 211 of the preliminary distributor channel 210 to be supplied, along said longitudinal axis L. Said feed pipes 220 are each arranged between two splash plates 222, which extend parallel to one another and which flank the outlet 221 of the respective feed pipe 220 on either side, and are each fixed in place on an assigned side wall 212 of the preliminary distributor channel 210 in question.

Furthermore, on the outwardly facing outsides of their side walls 212, at both sides of the cutouts 214 of the respective preliminary distributor channel 210, the preliminary distributor channels 210 have a baffle 216, these baffles 216 projecting vertically from the respective side wall 212 and each projecting, by a lower free end region, into the final distributor channel 202 arranged below the respective cutout 214. The baffles 216 serve to guide the flow of the liquid phase W', W" from the cutouts 214 of the preliminary distributor channels 210 into the assigned final distributor channels 202.

In order that the liquid phase W', W" in the two preliminary distributor channels 210 is always at the same level, the two preliminary distributor channels 210, in accordance with FIGS. 9 and 10, may be joined via at least one compensation channel 215, which is extended between the two preliminary distributor channels 210, specifically transversely with respect to them.

Figure 15:
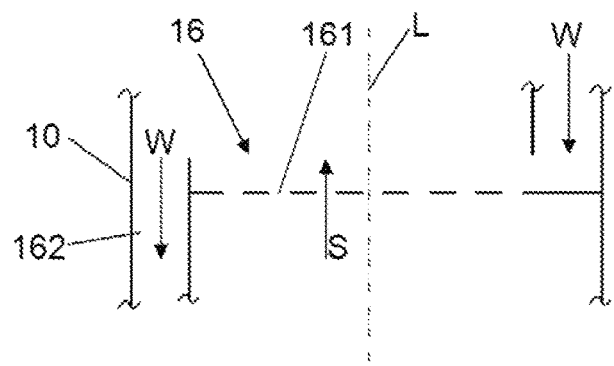
FIGS. 15 to 17 show schematic sectional representations of sieve, bubble cap and valve trays, respectively.
Figure 16:
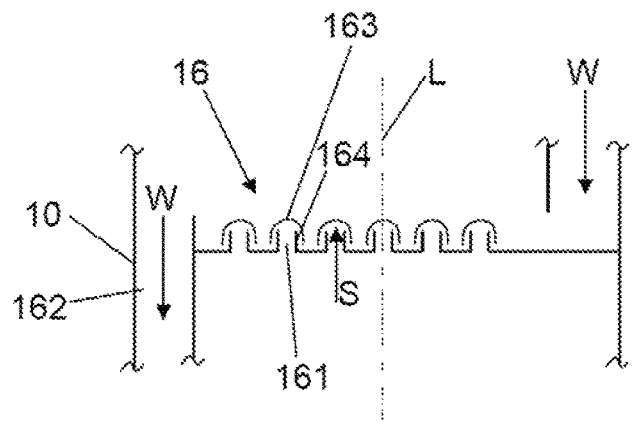
Figure 17:
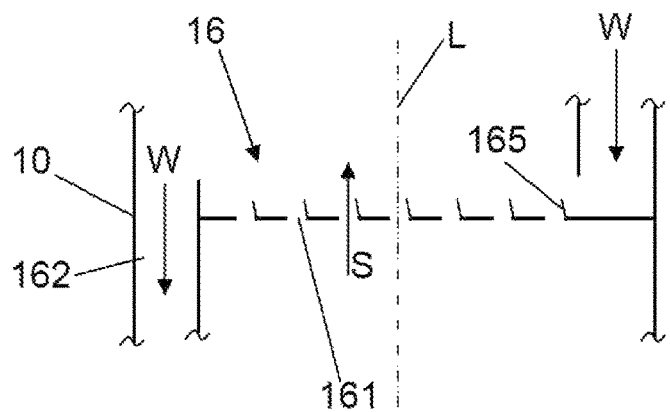

The abovementioned first mass transfer trays 16a, 16b, 16c of the petroleum spirit section 20 of the oil scrub column 1 are shown schematically in section in FIGS. 15 to 17. Sieve trays 16 as per FIG. 15 are column trays having a downcomer 162, via which the scrubbing medium W passes onto column trays situated beneath. These sieve trays 16 have a plurality of passages 161, through which the cracking gas S flows and contacts the scrubbing medium W located on the respective sieve tray 16.

In the case of first mass transfer trays in the form of bubble cap trays 16, in accordance with FIG. 16, again a downcomer 162 is provided. In the case of bubble cap trays 16, furthermore, said passages 161 are bordered by chimney necks 164, topped off with caps 163, and in particular the chimney necks 164 project into the respectively assigned cap 163.

Valve trays 16, in accordance with FIG. 17, may likewise have a downcomer 162. In the case of valve trays 16, furthermore, said passages 161 can be closed by valves 165, more particularly flaps, in order to prevent downpour. If the cracking gas pressure is sufficient, the valves are forced open, allowing the cracking gas S to flow from bottom to top through the passages 161 of the valve tray. Besides moveable valves, it is also possible to use fixed valves, i.e., fixed valve caps with a promoter effect.

| List of reference symbols | |
|---|---|
| 1 | Oil scrub column |
| 2 | Oil scrub column |
| 5 | Pump |
| 6 | Heat exchanger |
| 10 | Shell |
| 11 | Top |
| 12 | Bottoms |
| 13, 14 | Chimney tray |
| 15, 15a | Sieve or valve trays |
| 16, 16a, 16b, 16c | First mass transfer trays, e.g. sieve, bubble cap or valve trays |
| 17 | Side-to-side baffles |
| 20, 21, 21a, 21b | Sections of the column |
| 100 | Second mass transfer trays |
| 101 | Runoff element |
| 101a, 101b | Segments |
| 101c | Cap |
| 101d | End region |
| 102, 103 | Arms |
| 102a, 103a | Runoff surfaces |
| 104 | Edge |
| 110 | Carrier ring |
| 111 | Bearing |
| 112 | Bearer |
| 112a | Surface |
| 113 | End region |
| 115 | Cover plate |
| 161 | Passage |
| 162 | Downcomer |
| 163 | Cap |
| 164 | Chimney neck |
| 165 | Valve (more particularly flap) |
| 200, 300 | Liquid distributors |
| 201 | Cutouts |

-continued

| | List of reference symbols |
|---|---|
| 202 | Final distributor channel |
| 203 | Base |
| 204 | Side wall |
| 205 | Rim |
| 206 | Lower edge |
| 210 | Preliminary distributor channel |
| 211 | Base |
| 212 | Side wall |
| 213 | Rim |
| 214 | Cutout |
| 215 | Compensation channel |
| 216 | Baffle |
| 217 | Lower edge |
| 220 | Feed pipe |
| 221 | Cutout |
| 222 | Splash plate |
| F, F', F" | Fractions |
| I | Interior |
| L | Longitudinal axis |
| Q | Column cross section |
| S | Cracking gas stream |
| W, W', W" | Scrubbing media |

The invention claimed is:

1. A process for purification of a cracking gas stream in an oil scrub column having a shell extending along a longitudinal axis and enclosing an interior of the column, the interior being subdivided into a petroleum spirit section and an oil section arranged below the petroleum spirit section along the longitudinal axis, said process comprising:

introducing an amount of a cracking gas stream into the oil section wherein the cracking gas stream passes from bottom to top of the oil section along the longitudinal axis through second mass transfer trays of the oil section which are arranged one above another, and wherein a liquid, hydrocarbon-containing second scrubbing medium flows in said oil section in countercurrent to the cracking gas stream in order to separate out an oil fraction from the cracking gas stream, said second mass transfer trays each having a plurality of runoff elements extending parallel to and at a distance from one another, wherein each runoff element has first and second runoff surfaces along which a second scrubbing medium runs downward and which converge along the longitudinal axis towards the petroleum spirit section and meet, and in so doing form an edge extending transversely to the longitudinal axis, passing the cracking gas stream, after traversing the second mass transfer trays of the oil section, into the petroleum spirit section, wherein the cracking gas stream flows along the longitudinal axis from bottom to top of petroleum spirit section through first mass transfer trays of the petroleum spirit section, said first mass transfer trays being arranged one above another and being sieve trays, bubble trays and/or valve trays, and wherein a liquid, hydrocarbon-containing first scrubbing medium flows in said petroleum spirit section in countercurrent to the cracking gas stream in order to remove a petroleum spirit fraction from the cracking gas stream, withdrawing the cracking gas stream from a top of the petroleum spirit section, withdrawing the petroleum spirit fraction from the petroleum spirit section, recycling an amount of the petroleum spirit fraction as the first scrubbing medium into the top of the petroleum spirit section, wherein the amount of the petroleum spirit fraction recycled into the petroleum spirit section per unit time and the amount of the cracking gas introduced into the oil section per unit time are at a ratio of from 1:16 to 1:10.

2. The process according to claim 1, further comprising recycling a portion of the petroleum spirit fraction onto one of the first mass transfer trays.

3. The process according to claim 2, wherein said portion of the petroleum spirit fraction is recycled to the second-lowermost, third-lowermost or fourth-lowermost first mass transfer tray.

4. The process according to claim 1, wherein the petroleum spirit fraction is drawn off from a chimney tray that separates the petroleum spirit section from the oil section or from a lowermost first mass transfer tray that separates the petroleum spirit section from the oil section.

5. The process according to claim 1, wherein
said oil section is subdivided into a light oil section and a heavy oil section, which is arranged below said light oil section along the longitudinal axis, a plurality of second mass transfer trays are arranged in each of the light oil section and the heavy oil section, wherein the cracking gas stream is guided through the second mass transfer trays of the heavy oil section and subsequently through the second mass transfer trays of the light oil section, and
wherein the second mass transfer trays in the heavy oil section are supplied with a liquid, hydrocarbon-containing third scrubbing medium to separate out a heavy oil fraction from the cracking gas stream, and the second transfer trays in the light oil section are supplied with said liquid, hydrocarbon-containing second scrubbing medium to separate out a light oil fraction from the cracking gas stream.

6. The process according to claim 1, wherein the petroleum spirit section has 6 to 8 first mass transfer trays.

7. The process according to claim 1, wherein t the oil section has 10 to 20 second mass transfer trays.

8. The process according to claim 5, wherein the light oil section has 6 to 12 second mass transfer trays.

9. The process according to claim 5, wherein the heavy oil section has 4 to 8 second mass transfer trays.

10. The process according to claim 5, wherein
the oil scrub column has a first liquid distributor arranged in the light oil section, wherein by means of said first liquid distributor the second mass transfer trays are supplied with the second scrubbing medium, wherein the first liquid distributor introduces the second scrubbing medium onto the edges of the runoff elements of an uppermost second mass transfer tray of the light oil section so that the second scrubbing medium flows off from the respective runoff element via the runoff surfaces at both sides of the respective edge,
the oil scrub column has a second liquid distributor is arranged in the heavy oil section, wherein by means of said second liquid distributor the second mass transfer trays of the heavy oil section are supplied with the third scrubbing medium, wherein the second liquid distributor introduces the third scrubbing medium onto the edges of the runoff elements of an uppermost second mass transfer tray of the heavy oil section, so that the third scrubbing medium flows off from the respective runoff element via the runoff surfaces at both sides of the respective edge.

11. The process according to claim 10, wherein the first and/or the second liquid distributors each have a plurality of cutouts through which the respective scrubbing medium is introduced onto the edges of the runoff elements of the respective uppermost second mass transfer tray, where the cutouts are each arranged perpendicularly above an edge of an assigned runoff element.

12. The process according to claim 10, wherein the first and/or the second liquid distributors each have a plurality of final distributor channels which extend along the column cross section and extend transversely to the runoff elements.

13. The process according to claim 12, wherein the final distributor channels each have a base which extends transversely to the longitudinal axis, and two side walls starting from said base, where said side walls each have an upper rim, and where the cutouts are designed in the form of vacancies at the upper rim of each sidewall.

14. The process according to claim 13, wherein the first and/or second liquid distributors have at least two preliminary distributor channels, which are parallel to one another and arranged above the final distributor channels along the longitudinal axis, wherein said final distributor channels are charged with the respective scrubbing medium by means of said preliminary distributor channels, and wherein the preliminary distributor channels extend along the column cross section and extend transversely to the final distributor channels.

15. The process according to claim 14, wherein each of the preliminary distributor channels each has a base which extends transversely to the longitudinal axis, and two side walls starting from said base, where said side walls each have an upper rim, at which cutouts are designed in the form of vacancies via which the respective scrubbing medium is led into respectively one assigned final distributor channel, wherein these cutouts of the preliminary distributor channels are arranged in each case perpendicularly above an assigned final distributor channel, and the preliminary distributor channels are connected to one another via at least one compensation channel.

16. The process according to claim 1, wherein the amount of the petroleum spirit fraction recycled into the petroleum spirit section per unit time and the amount of the cracking gas introduced into the oil section per unit time are at a ratio of 1:12 to 1:10.

17. The process according to claim 5, wherein the light oil section is separated from the heavy oil section by a chimney tray.

18. The process according to claim 6, wherein adjacent first mass transfer trays have a distance from one another along the longitudinal axis in the range from 500 mm to 900 mm.

19. The process according to claim 1, wherein the oil scrub column has a first liquid distributor arranged in the oil section, wherein by means of said first liquid distributor the second mass transfer trays are supplied with the second scrubbing medium, wherein the first liquid distributor introduces the second scrubbing medium onto the edges of the runoff elements of an uppermost second mass transfer tray of the oil section so that the second scrubbing medium flows off from the respective runoff element via the runoff surfaces at both sides of the respective edge.

20. The process according to claim 5, wherein a light oil fraction is withdrawn from the light oil section and at least part of the light oil fraction is recycled to the light oil section as the second scrubbing medium or as part of the second scrubbing medium.

21. The process according to claim 20, part of petroleum spirit fraction withdrawn from the petroleum spirit section is added to the light oil fraction withdrawn from the light oil section to form a mixture, and this mixture is recycled as the second scrubbing medium into the light oil section.

22. The process according to claim 5, wherein a heavy oil fraction is withdrawn from the bottom of the oil scrub column and at least part of the heavy oil fraction is recycled to the heavy oil section as the third scrubbing medium.

23. The process according to claim 1, wherein the length of the petroleum spirit section is not more than half the length of the oil section.

24. The process according to claim 1, wherein adjacent second mass transfer trays of the oil section have a distance from one another along the longitudinal axis in the range from 500 mm to 900 mm.

* * * * *